United States Patent [19]

Bellet et al.

[11] Patent Number: 5,011,771
[45] Date of Patent: Apr. 30, 1991

[54] MULTIEPITOPIC IMMUNOMETRIC ASSAY

[75] Inventors: Dominique Bellet, Paris, France; Jack R. Wands, Waban, Mass.

[73] Assignee: The General Hospital Corporation, Boston, Mass.

[21] Appl. No.: 102,766

[22] Filed: Sep. 24, 1987

Related U.S. Application Data

[63] Continuation-in-part of Ser. No. 599,560, Apr. 12, 1984, abandoned.

[51] Int. Cl.$^5$ .................. C12N 5/00; G01N 33/53; G01N 33/545; C12Q 1/00
[52] U.S. Cl. ................ 435/7.94; 435/240.77; 435/975; 436/531; 436/535; 436/548; 436/800; 436/804; 436/868; 436/819; 436/813; 436/814; 436/815
[58] Field of Search ............... 435/7, 240.27, 810; 436/531, 535, 548, 800, 804, 808, 819, 813-815

[56] References Cited

U.S. PATENT DOCUMENTS

| 4,223,002 | 9/1980 | Newman | 424/1 |
| 4,361,647 | 11/1982 | Remington et al. | 935/108 X |
| 4,376,110 | 3/1983 | David et al. | 935/110 X |
| 4,471,058 | 9/1984 | Smith et al. | 935/110 X |
| 4,474,892 | 10/1984 | Murad | 436/513 |
| 4,486,530 | 12/1984 | David et al. | 435/7 |
| 4,514,505 | 5/1985 | Canfield et al. | 436/500 |
| 4,565,687 | 1/1986 | Kjazaeli et al. | 436/548 |

FOREIGN PATENT DOCUMENTS

| 0048357 | 1/1981 | | |
| 38362 | 10/1981 | European Pat. Off. | 435/240 |
| 038642 | 10/1981 | European Pat. Off. | . |
| 42755 | 12/1981 | European Pat. Off. | 436/531 |
| 45103 | 2/1982 | European Pat. Off. | 436/548 |
| 62892 | 10/1982 | European Pat. Off. | 435/7 |
| 8108105 | 10/1981 | France | . |
| WO83/04312 | 12/1983 | PCT Int'l Appl. | . |
| WO85/02258 | 5/1985 | PCT Int'l Appl. | . |
| 2074727 | 11/1981 | United Kingdom | . |
| 2095831 | 11/1982 | United Kingdom | . |

OTHER PUBLICATIONS

Bidurt, et al., J. Immunol 134, pp. 457-464, 1985.
Goldstein, et al, J. Inf. Diseases 147, pp. 829-837, 1983.
Henchal, et al, J. Virol 68(3), pp. 845-851, 1987.
Rugg et al, Clin. Chem. 32(10): 1844-1848 (1986).
Shimizu et al., Clin. Chem. 28(3): 546-547 (1982).
Caraux et al, J. Immunol. 134(2): 835-840 (1985).
Longhi et al., J. Immunol. Meth. 92(1): 89-95 (1986).
Bellet et al., J. Clin. Endoc. and Metab. 63(6): 1319-1327 (1986).
Armstrong et al., J. Clin. Endoc. and Metab. 59(5): 867-874 (1984).
Mizuchi et al., J. Immunol. Methods 74(1): 369-374 (1984).
Bellet et al., Endocrinol. 115(1): 330-336 (1984).
Brock, David J. H., et al., Clinica Chimica Acta 122: 353-358 (1982).

(List continued on next page.)

Primary Examiner—Robert A. Wax
Assistant Examiner—Bradley L. Sisson
Attorney, Agent, or Firm—Sterne, Kessler, Goldstein & Fox

[57] ABSTRACT

The invention relates to an immunometric assay for a multivalent antigen in a sample which comprises forming a complex of the antigen together with multiple immobilized monoclonal antibodies against different epitopes of the antigen and with a detectably labeled soluble monoclonal antibody which is identical to one of the multiple immobilized antibodies. The labeled antibody associated with the complex is separated from the remaining soluble antibody and the detectably labeled antibody associated with the complex or unassociated with the complex is detected. Any one of the multiple immobilized monoclonal antibodies shows, by itself, substantially less binding towards the antigen in the immunometric assay, when used with itself or another monocolonal antibody in soluble labeled form, than when used with the multiple immobilized antibodies in combination.

12 Claims, 6 Drawing Sheets

OTHER PUBLICATIONS

Porstmann, T., et al., Clinica Chimica Acta 135: 13–22 (1983).

Nomura, M., et al., Journal of Immunological Methods 58: 292–300 (1983).

Hunter, W. M., et al., Journal of Immunological Methods 50: 133–144 (1982).

Van Heyningen, V., et al., Journal of Immunological Methods 50: 123–131.

Nomura, M., et al., Journal of Immunological Methods 56:13–17 (1983).

Porstmann, B., et al,. Journal of Immunological Methods 66: 179–185 (1984).

Uotila, M., et al., Journal of Immunological Methods 42: 11–15 (1981).

Ehrlich, P. H., et al., Journal of Immunology 128: 2709–2713 (1982).

Ehrlich, P. H., et al, Journal of Immunology 131: 1906–1912 (1983).

Sterman, N., et al., The Lancet, 1983, 647–649.

Shapiro, A. I., et al., American Journal of Obstetrics and Gynecology 148: 72–76 (1984).

Stewart, M. C., et al., Journal of Endocrinology 98: 323–330 (1983).

Bosch, A. M. G., et al., Protides of the Biological Fluids, vol. 29, pp. 837–842 (1982).

Schroeder, J., et al., Pregnancy Proteins: Biological, Chemical and Clinical Applications, pp. 69–76 (1982).

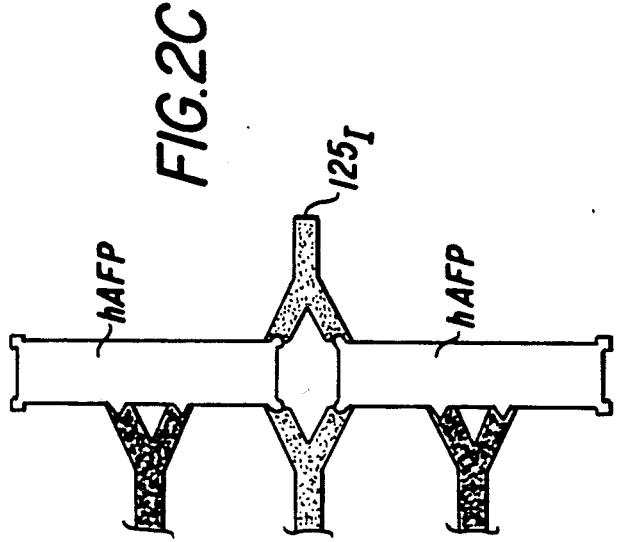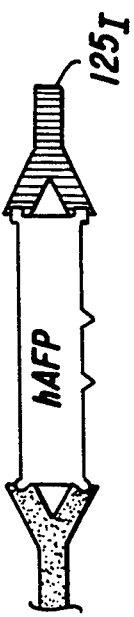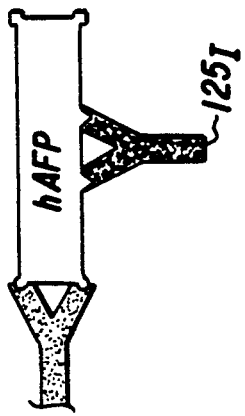

MULTIEPITOPIC IMMUNOMETRIC ASSAY

The present invention was made utilizing funds of the U.S. Government. The U.S. Government is therefore granted a royalty-free, nonexclusive, worldwide, paid-up license in this invention.

The present application is a continuation-in-part of application Ser. No. 599,560, filed Apr. 12, 1984, now abandoned.

BACKGROUND OF THE INVENTION

1. Field of the Invention

The present invention relates to an immunometric assay using monoclonal antibodies for the detection and/or determination of the levels of multiepitopic antigens, such as, for example, alpha-feto protein or human chorionic gonadotropin.

2. Brief Description of the Background Art

Immunometric assays (also called "sandwich" assays) using monoclonal antibodies for the determination of the presence and/or concentration of antigenic substances in fluids are well known. For example, David et al. U.S. Pat. No. 4,376,110 suggests that this type of assay is useful for the determination of a variety of polyvalent antigenic substances against which antibodies can be produced. David et al. mention, among others, hepatitis A and B, IgE and alpha-fetoprotein. The assays are described in the simultaneous, reverse and forward modes, and specifically exemplified for the determination of IgE.

Alpha-fetoprotein (AFP) is a major serum protein synthesized by fetal liver cells, yolk sac cells, and in trace amounts by the fetal gastrointestinal tract. Reappearance of AFP in adult serum often signals pathologic conditions, particularly the presence of hepatocellular carcinomas (HCC) and germ cell tumors containing yolk sac cell elements. Although existing assays may be successfully used for monitoring treatment of AFP-producing tumors and as an independent prognostic tool, the finding of elevated serum AFP levels in some patients with nonmalignant liver diseases, particularly in acute and chronic viral hepatitis and cirrhosis, has limited the value of such assays as an independent specific test to establish the diagnosis of cancer.

An important goal in current AFP research is to improve the cancer specificity of the test, particularly given the need for early detection of HCC in high risk populations.

Commercial assays for alpha-feto protein have involved the use of polyvalent sera with all of the attendant limitations and problems. Published immunoassays using monoclonal antibodies against AFP include those of Portsman, T. et al., Clin. Chim. Acta. 135:13–22 (1983); Brock, D. J. et al., ibid, 122:353-8 (1982); Uotila, M., et al , J. Imm. Methods, 42:11–15 (1981); Hunter, W. M. et al , ibid, 50:133–144 (1982); Van Heyningen, V., et al, ibid, 50:123–131 (1982); Nomura, M. et al, ibid, 56:13–17 (1983); Nomura, M. et al., ibid, 58:293–300 (1983); Portsmann, B. et al., ibid, 66:173–185 (1984) Engvall et al. in European Patent Application 0048357, published Mar. 31, 1982, also describe a sandwich assay for AFP which may utilize two different monoclonal antibodies, one on a solid phase and the other in soluble labelled form.

These previously described immunoassays for AFP are of two types. First, a two site immunoassay based on two monoclonal antibodies directed against two separate and distinct epitopes, one of these antibodies on a solid phase and the other in soluble labelled form. Second, a three site immunoassay based on three monoclonal antibodies directed against three separate and distinct epitopes, one of these antibodies on a solid phase and both others in soluble labelled form. None of the data has reported a three site immunoassay based on two different monoclonal antibodies directed against two distinct and separate epitopes on said antigen, the first of these antibodies on a solid phase, and the second on the solid phase and in soluble labelled form.

One of the problems with many prior art assays is that heretofore it has not been possible to use serum AFP levels as a screening assay for HCC, since most patients with acute and chronic active hepatitis (with and without cirrhosis) often show AFP elevations up to 1,000 ng/ml, and sometimes greater than 5,000 ng/ml. Thus, the diagnosis of HCC can only be suspected in patients with AFP levels above 400–1,000 ng/ml, and other methods are required to confirm the diagnosis. In addition, often at the time of diagnosis, the size of the tumor is already too large and/or the cirrhosis too far advanced to warrant consideration of surgical resection. In a few patients, the discovery of an elevated AFP has led to curative resections of small tumors.

An acute need therefore still exists in the art for an assay for AFP levels which is selective for patients with HCC and can distinguish over those where the levels of AFP are higher than those related to non-HCC causes, such as cirrhosis or hepatitis.

Human chorionic gonadotropin (HCG) is a hormone secreted by the placenta shortly after the start of pregnancy. It can be measured by radioimmunoassay, and detected in the blood as early as 6 days after conception. Its presence in the urine in early pregnancy is the basis for various laboratory tests for pregnancy, and it can sometimes be detected in the urine as early as 14 days after conception.

Assays for such important antigens as AFP, HCG and others are in constant need of improvement, both in sensitivity and selectivity.

SUMMARY OF THE INVENTION

The present invention arose out of the discovery that the sensitivity of total monoclonal sandwich assays for multivalent antigens can be greatly increased if multiple (e.g., at least two) antibodies, each against a different epitope on said antigen, are immobilized on the solid phase, and at least one soluble labelled monoclonal antibody is identical with one of the immobilized antibodies, and wherein only such combination shows high binding characteristics.

In the invention, any one of the immobilized antibodies alone shows good to average or even perhaps poor binding to the antigen when tested in a sandwich assay by itself, using the same or different antibody in labelled soluble form. Greatly increased sensitivity, however, is brought about by the relationship between the binding of the combination of multiple different antibodies on the solid phase (high), and that of any single one (substantially none). This is brought about by the "appearance" or "presentation," upon immobilization of the antigen on the solid phase via the antibodies, of an additional epitope or epitopes. This new epitope or epitopes allows substantial binding of the soluble, detectably labelled antibody to the immobilized antigen.

This phenomenon dramatically increases the selectivity and sensitivity of the assay, since it distinguishes over similar polyvalent antigens which already carry in their soluble state (i.e., while not bound to the solid phase via the antibodies) the additional epitopes needed to provide high binding to the soluble antibody. Very fine epitopic differences can be obtained with the present assay.

Thus the present invention provides an immunometric assay for a multivalent antigen in a sample which comprises:

forming a complex of said antigen together with
  (A) multiple immobilized monoclonal antibodies against different epitopes on said antigen; and with
  (B) a detectably labelled monoclonal soluble antibody which is one of said multiple immobilized antibodies;

separating labelled antibody associated with said complex from soluble labelled antibody; and detecting either said labelled antibody associated with said complex, or said unassociated labelled antibody; wherein any one of said multiple immobilized monoclonal antibodies shows, by itself, substantially less binding towards said antigen in said immunometric assay when used with itself or another monoclonal antibody in soluble labelled form, than said multiple immobilized antibodies in combination.

As an example, after screening various different anti-AFP monoclonal antibodies and various combinations and permutations thereof, it was discovered that one specific combination of two antibodies in a total monoclonal immunometric assay for AFP yields sensitivities heretofore unobtainable with prior art assays for AFP. This is obtained only upon using at least two different monoclonal antibodies against AFP on an insoluble solid phase, and using one of said two antibodies in a soluble, detectably labelled form. A sandwich assay is then carried out with this configuration.

If the AFP assay uses only one immobilized monoclonal antibody together with the same or different antibody in soluble labelled form, the binding for AFP in the assay is substantially less. It is the synergistic combination of multiple different antibodies on the solid phase showing substantial binding, whereas any one of them does not, that lies at the heart of the invention.

Quite surprisingly and unexpectedly, the AFP assay shows four to ten times more sensitivity than commercially available conventional polyvalent immunoassays, and it has a lower level of sensitivity of approximately 0.5 ng/ml. Most importantly, however, the AFP assay is capable of discriminating between AFP-producing carcinomas (especially HCC) and various benign liver diseases. In the AFP assay of the invention, the incidence of AFP elevation was extremely low in normal individuals in a number of different disease categories. Thus, no healthy subject had a level above 5 ng/ml, whereas other reports have shown 75% of normal human sera to have AFP levels greater than 5 ng/ml (see, for example, Ruohslati, E., et al., *Nature* 235:161–162 (1972) and Ruohslati, E., et al., *International Journal of Cancer* 8:374–383 (1971)). It is also noteworthy that 98% or so of HBsAg chronic carriers had a serum AFP level below 5 ng/ml and 100% had levels below 10 ng/ml. It is also striking with the AFP assay that about 95% of patients with miscellaneous liver disorders and other disease controls had AFP levels below 5 ng/ml with greater than 99% below 20 ng/ml. Most surprising was the finding that in cirrhotic patients (regardless of the etiology of the cirrhosis or their geographical origin), only about 3% had an AFP level above 20 ng/ml, and none had levels above 100 ng/ml. Thus, the AFP assay of the present invention demonstrates remarkable specificity for AFP-producing tumors and, depending on the cutoff value for AFP-positive results, these patients show little overlap with non-malignant liver disorders and other disease controls.

Thus, in a specific embodiment of the invention, there is provided an immunometric assay for alpha-feto protein in a sample which comprises:

forming a complex of said alpha-feto protein together with
  (a) at least two immobilized monoclonal antibodies the first of said antibodies, having the identifying characteristics of an antibody obtained from cell line I-295; and the second of said antibodies having the identifying characteristics of an antibody obtained from cell line I-296; and with
  (b) at least one detectably labelled soluble antibody which is said first antibody;

separating labelled antibody associated with said complex from soluble labelled antibody; and detecting either said labelled antibody associated with said complex, or said unassociated labelled antibody.

The invention also provides an immunometric assay for HCG utilizing the principles enunciated above, i.e., with multiple immobilized monoclonal antibodies, and a soluble labelled antibody which is one of said immobilized antibodies, and wherein any one of the immobilized antibodies alone shows substantially no binding in the assay.

BRIEF DESCRIPTION OF THE DRAWINGS

FIG. 2 shows an alternative hypothetical model which may also explain the results. In this model the antibody immobilized on the solid phase support is incapable of detecting the antigen due to limitation of available specific binding sites (epitopes). However, a second soluble radio-labelled antibody which recognizes a different epitope may identify the antigen (FIGS. 2A and 2B). If, for example, two monoclonal antibodies, each of which recognizes a different epitope are immobilized on the solid phase support, the one monoclonal antibody shown immobilized in FIG. 2A, heretofore not capable of recognizing said antigen is now able to bind to the antigen in the soluble radiolabeled form, due to the unique presentation of an epitope by the combination of antibodies in the solid phase support (FIG. 2C).

Note: The representations of FIGS. 1 and 2 are, as indicated, hypothetical. They may prove to be incomplete or subject to future refinement. Applicants do not wish to be bound by these depictions, and present them only since they may aid in the understanding of the invention.

Figure 1A:
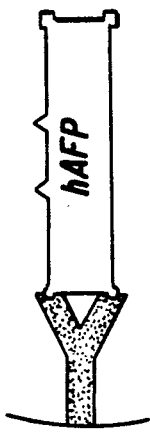
FIG. 1 shows one of several hypothetical models which may explain the results observed in the present invention, wherein hAFP stands for human alpha-feto protein, and the detectably labelled soluble antibody is labelled with $^{125}$I. Upon bonding of hAFP to the insoluble phase via the first antibody, no epitopes bonding with antibody I become available (FIG. 1A). However, upon bonding of hAFP to the soluble phase by both antibody I and antibody II (FIGS. 1B and 1C), a pair of epitopes recognizable by antibody I appear due to a conformational change (FIG. 1D). Thereafter, detectably labelled antibody I can bind to the hAFP.
(FIG. 1D)
Figure 1B:
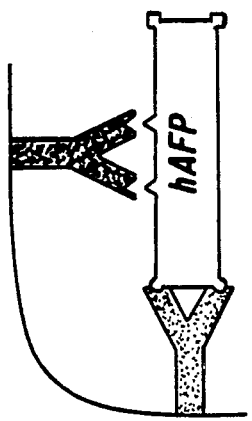
Figure 1C:
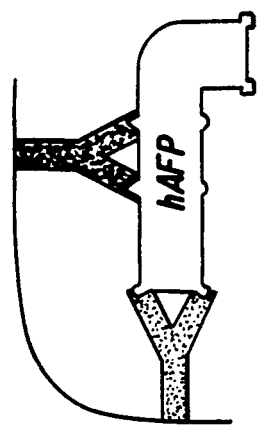
Figure 1D:
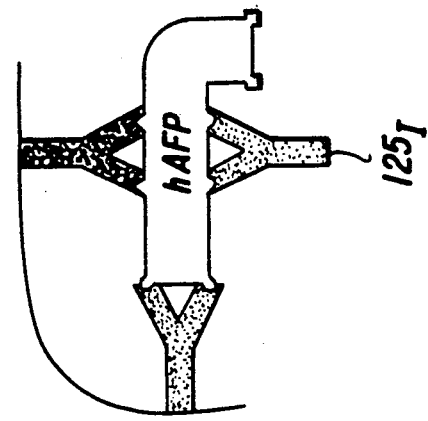
Figure 3:
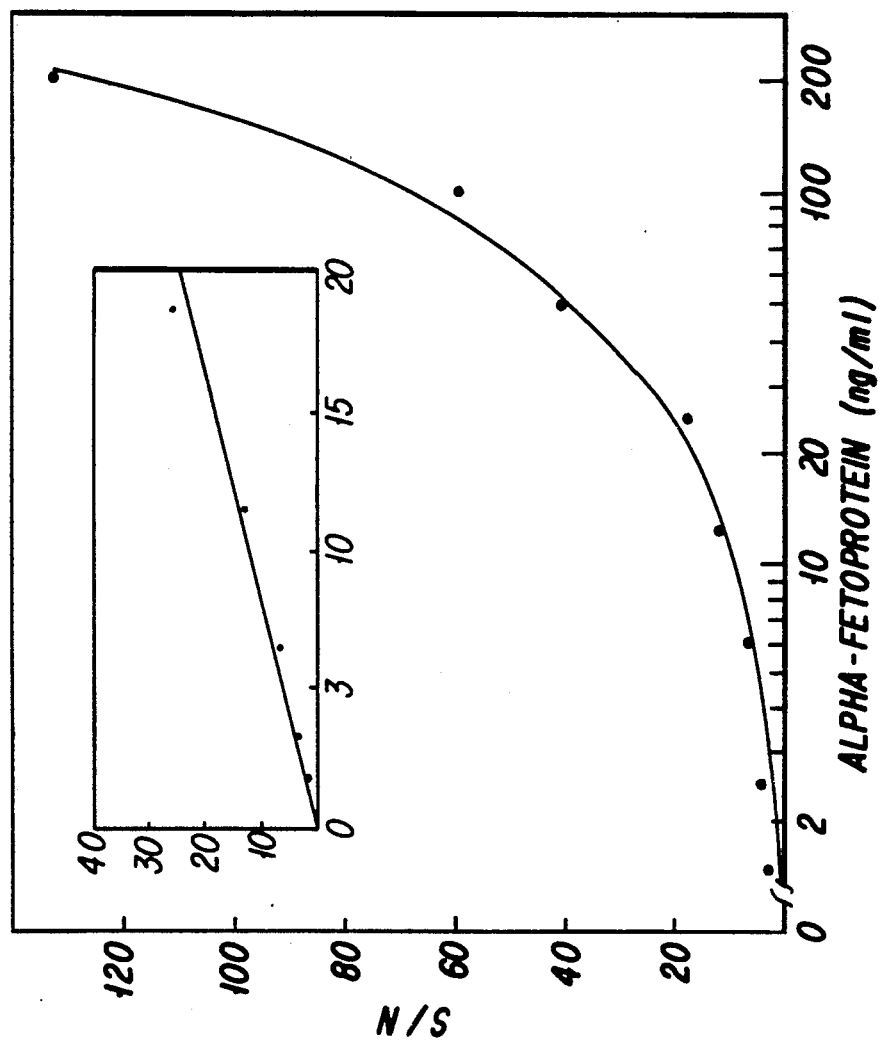

FIG. 3 represents a monoclonal immunometric assay for alpha-feto protein with two standard curves. The insert emphasizes the linear portion of the curve between 1.5 and 20 ng/ml. The assay is a "simultaneous sandwich" immunoassay and is performed at 45° C. for one hour. S/N represents the signal-to-noise ratio defined as cpm bound in experimental samples divided by the mean of the negative controls.

Figure 4:
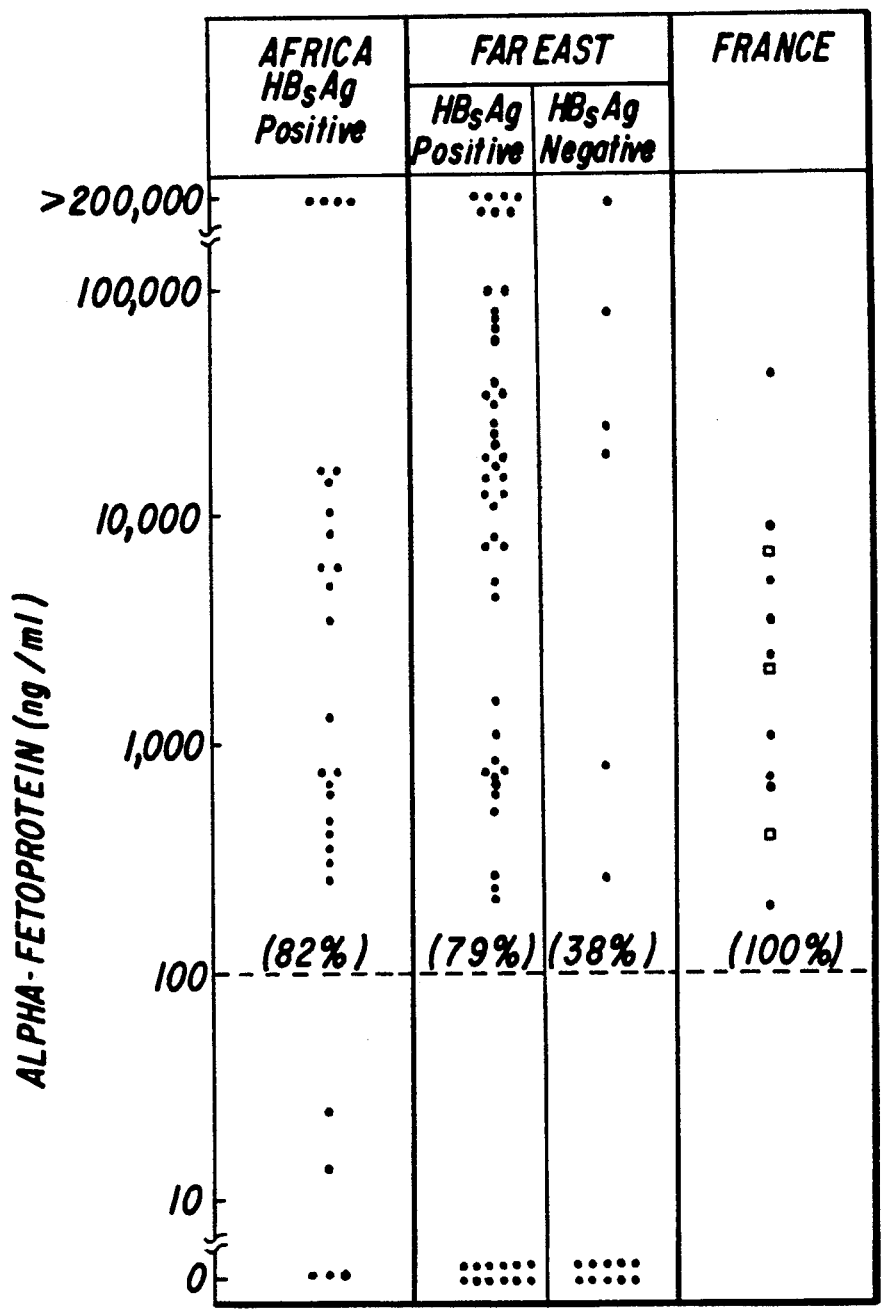

FIG. 4 represents the absolute AFP values in patients with HCC(●) or hepatoblastoma (□) from Africa, the Far East and France. The numbers in parentheses represent the percent of individuals with AFP levels greater than 100 ng/ml.

Figure 5:
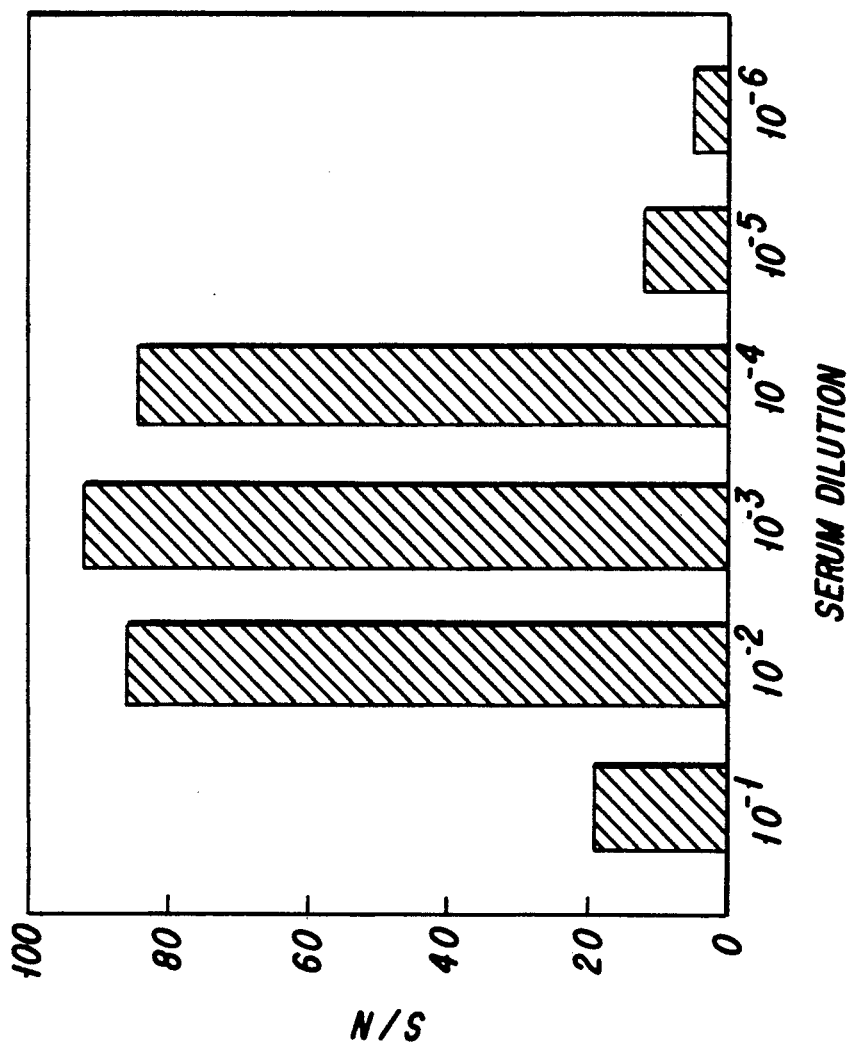

FIG. 5 represents a typical result of serial dilution of serum from a strongly AFP positive patient with HCC. This shows the "hook effect" using the simultaneous sandwich monoclonal immunoassay.

Figure 6:
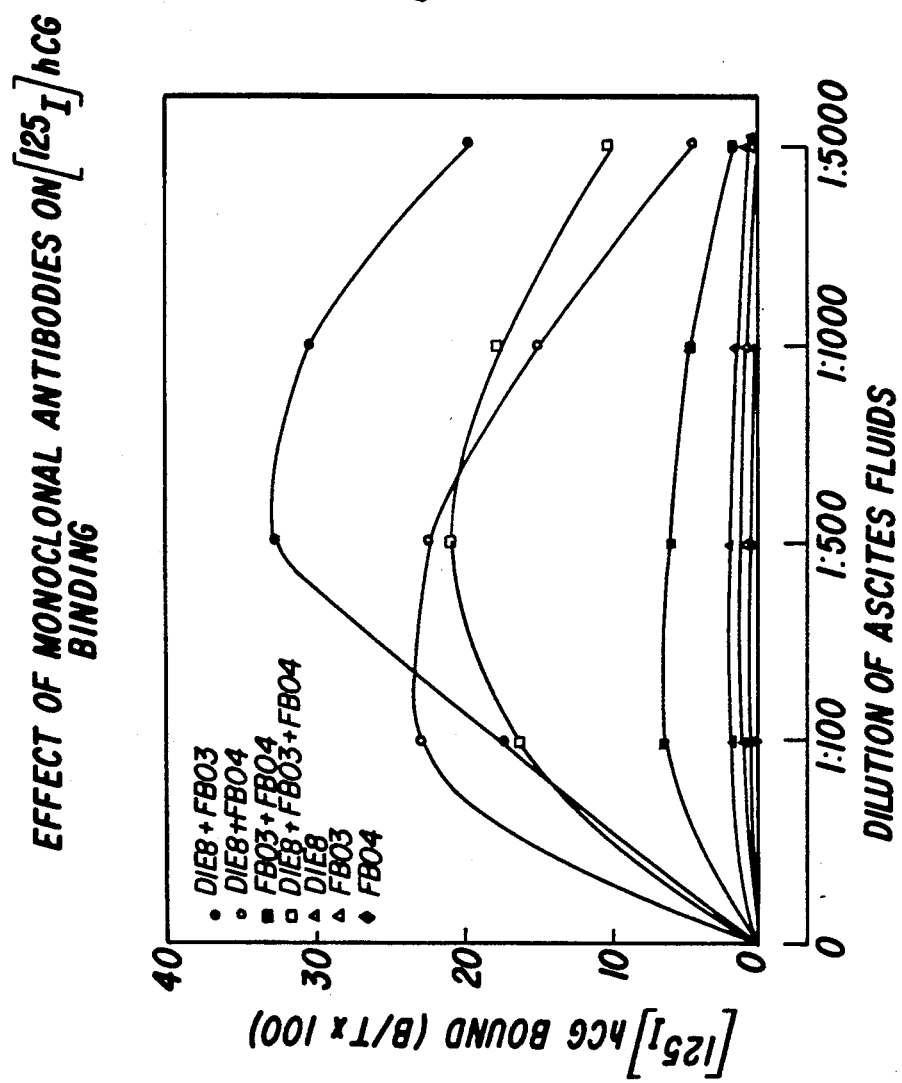

FIG. 6 illustrates the binding of hCG by monoclonal antibodies D1E8, FB03 and FB04 alone or in combination.

BRIEF DESCRIPTION OF THE PREFERRED EMBODIMENT

By the term "immunometric assay" or "sandwich immunoassay," it is meant to include simultaneous sandwich, forward sandwich and reverse sandwich immunoassays. These terms are well understood to those skilled in the art.

In a forward sandwich immunoassay, a sample is first incubated with a solid phase immunoabsorbent containing multiple different monoclonal antibodies against the antigen. Incubation is continued for a period of time sufficient to allow the antigen in the sample to bind to the immobilized antibodies in the solid phase. After the first incubation, the solid phase immunoabsorbent is separated from the incubation mixture and washed to remove excess antigen and other interfering substances, such as non-specific binding proteins, which also may be present in the sample. Solid phase immunoabsorbent containing antigen bound to the immobilized antibodies is subsequently incubated for a second time with soluble labelled antibody or antibodies. After the second incubation, another wash is performed to remove unbound labelled antibody(ies) from the solid phase immunoabsorbent and removing non-specifically bound labelled antibody(ies). Labelled antibody(ies) bound to the solid phase immunoabsorbent is then detected and the amount of labelled antibody detected serves as a direct measure of the amount of antigen present in the original sample. Alternatively, labelled antibody which is not associated with the immunoabsorbent complex can also be detected, in which case the measure is in inverse proportion to the amount of antigen present in the sample. Forward sandwich assays are described, for example, in U.S. Pat. Nos. 3,867,517; 4,012,294 and 4,376,110.

In carrying out forward immunometric assays, the process comprises, in more detail:
(a) first forming a mixture of the sample with the solid phase bound antibodies and incubating the mixture for a time and under conditions sufficient to allow antigen in the sample to bind to the solid phase bound antibodies;
(b) adding to the mixture after said incubation of step (a) the detectably labelled antibody or antibodies and incubating the new resulting mixture for a time and under conditions sufficient to allow the labelled antibody to bind to the solid phase immunoabsorbent;
(c) separating the solid phase immunoabsorbent from the mixture after the incubation in step (b); and
(d) detecting either the labelled antibody or antibodies bound to the solid phase immunoabsorbent or detecting the antibody not associated therewith.

In a reverse sandwich assay, the sample is initially incubated with labelled antibody(ies), after which the solid phase immunoabsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110.

In carrying out reverse immunometric assays, the process comprises, in more detail:
(a) first forming a mixture of the sample with the soluble detectably labelled antibody for a time and under conditions sufficient to allow antigen in the sample to bind to the labelled antibody;
(b) adding to the mixture after the incubation of step (a) the solid phase bound antibodies and incubating the new resulting mixture for a time and under conditions sufficient to allow antigen bound to the labelled antibody to bind to the solid phase antibodies;
(c) separating the solid phase immunoabsorbent from the incubation mixture after the incubation in step (b); and
(d) detecting either the labelled antibody bound to the solid phase immunoabsorbent or detecting the labelled antibody not associated therewith.

In a simultaneous sandwich assay, the sample, the immunoabsorbent having multiple immobilized antibodies thereon and labelled soluble antibody or antibodies are incubated simultaneously in one incubation step. The simultaneous assay requires only a single incubation and has a lack of washing steps. The use of a simultaneous assay is by far the preferred one. This type of assay brings about ease of handling, homogeneity, reproducibility, linearity of the assays and high precision. The sample containing antigen, solid phase immunoabsorbent with immobilized antibodies and labelled soluble antibody or antibodies are incubated under conditions and for a period of time sufficient to allow antigen to bind to the immobilized antibodies and to the soluble antibody(ies). In general, it is desirable to provide incubation conditions sufficient to bind as much antigen as possible, since this maximizes the binding of labelled antibody to the solid phase, thereby increasing the signal. Typical conditions of time and temperature are two hours at 45° C., or twelve hours at 37° C.

Labelled antibody typically binds to antigen more rapidly than immobilized antibodies, since the former is in solution whereas the latter are bound to the solid phase support. Because of this, labelled antibody may be employed in a lower concentration than immobilized antibodies, and it is also preferable to employ a high specific activity for labelled antibody. For example, labelled antibody might be employed at a concentration of about 1–50 ng/per assay, whereas immobilized antibodies might have a concentration of 10–500 ng/per assay per antibody. The labelled antibody might have a specific activity with, for instance, one radioiodine per molecule, or as high as two or more radioiodines per molecule of antibody.

Of course, the specific concentrations of labelled and immobilized antibodies, the temperature and time of incubation as well as other such assay conditions can be varied, depending on various factors including the concentration of antigen in the sample, the nature of the sample, and the like. Those skilled in the art will be able to determine operative and optimal assay conditions for each determination by employing routine experimentation.

After the single incubation period, the solid phase immunoabsorbent is removed from the incubation mixture. This can be accomplished by any of the known separation techniques, such as sedimentation and centrifugation. A washing step is not required prior to detection of bound labelled antibody. Detection can be performed by a scintillation counter, for example, if the label is a radioactive gamma-emitter, or by a fluorometer, for example, if the label is a fluorescent material. In the case of an enzyme label, the detection can be done by colorimetric methods employing a substrate for the enzyme.

In carrying out the simultaneous immunometric assay on a sample containing a multivalent antigen, the process comprises, in more detail:

(a) simultaneously forming a mixture comprising the sample, together with the solid phase bound antibodies and the soluble labelled antibody or antibodies;

(b) incubating the mixture formed in step (a) for a time and under conditions sufficient to allow antigen in the sample to bind to both immobilized and labelled antibodies;

(c) separating the solid phase immunoabsorbent from the incubation mixture after the incubation; and (d) detecting either labelled antibody bound to the solid phase immunoabsorbent or detecting labelled antibody not associated therewith.

Other such steps as washing, stirring, shaking, filtering and the like may of course be added to the assays, as is the custom or necessity for any particular situation.

In the preferred mode for performing the assays it is important that certain "blockers" be present in the incubation medium (usually added with the labelled soluble antibody). The "blockers" are added to assure that non-specific proteins, proteases, or human antibodies to mouse immunoglobulins present in the experimental sample do not cross-link or destroy the monoclonal antibodies on the solid phase support, or the radiolabelled indicator antibody, to yield false positive or false negative results. The selection of "blockers" therefore adds substantially to the specificity of the assays described in the present invention. It has been found that a number of nonrelevant (i.e. non specific) monoclonal antibodies of the same class or subclass (isotype) as those used in the assays (e.g. $IgG_1$, $IgG_{2a}$, IgM, etc.) can be used as "blockers." The concentration of the "blockers" (normally 1-100 microgs/microl) is important, in order to maintain the proper sensitivity yet inhibit any unwanted interference by mutually occuring cross reactive proteins in human serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01-10 microgs/ml) to the buffer which contains the "blockers."

There are many solid phase immunoabsorbents which have been employed and which can be used in the present invention. Well known immunoabsorbents include beads formed from glass, polystyrene, polypropylene, dextran, nylon and other materials; tubes formed from or coated with such materials, and the like. The immobilized antibodies can be either covalently or physically bound to the solid phase immunoabsorbent, by techniques such as covalent bonding via an amide or ester linkage, or by absorption. It is important that the multiple immobilized antibodies be bound to the same solid phase since close proximity is important. This can be readily achieved by either simultaneous or sequential binding of each antibody on the same solid phase. Those skilled in the art will know many other suitable solid phase immunoabsorbents and methods for immobilizing antibodies thereon, or will be able to ascertain such, using no more than routine experimentation.

The monoclonal antibody which remains in the soluble state, and is used as the detectably labelled antibody can be a single antibody or a mixture thereof At least one soluble antibody must be identical to one of the immobilized ones. The soluble antibody can be labelled with any detectable label, such as a radiolabel, a fluorescent label, an enzyme label, a free radical label or a bacteriophage label. Most commonly, the label is a radiolabel (radioimmunoassay) or an enzyme label (enzyme immunoassay). The more common radiolabels are $^{125}I$, $^{131}I$, $^{3}H$ and $^{14}C$. Among the common enzyme labels are horseradish peroxidase, alkaline phosphatase, beta-D-galactosidase, glucose oxidase and glucoamylase. Among the fluorescent materials are, for example, fluorescein isothiocyanate, and rhodamine.

Any animal sample containing a detectable yet unknown amount of antigen can be used. Such sample is normally from a human and may be liquid (such as, for example, urine, saliva, blood, serum and the like), or solid or semi-solid (tissues, feces, and the like).

The term "epitope" as used in this invention is meant to include any antigenic determinant of an antigen responsible for specific interaction with antibody molecules elicited by the same or related antigen. Antigenic determinants usually consist of chemically active surface groupings of molecules such as amino acids or sugar side chains. The epitopes have specific three dimensional structural characteristics as well as specific electronic characteristics.

The antigens capable of determination using the process of the present invention are so-called "multivalent antigens." A multivalent antigen is meant to include an antigen having at least two different epitopes capable of specific interaction with antibody binding sites, (the antibody binding sites are also called paratopes). Normally, the antigen determinable by this invention carries a multiplicity of epitopes, with the proviso that at least two of them have different immunodominant points. Furthermore, it is necessary that at least the two different epitopes be sufficiently separated from one another so as to allow simultaneous binding of a different immobilized antibody to each of said epitopes. If the epitopes are too close, steric interference may arise, and the immunoassay is complicated. Normally, it is required that the minimum distance between two epitopes on the multivalent antigen be about 15-20A.

Any multivalent antigen as defined above can be detected by the method of the present invention. This includes viral antigens such as hepatitis B surface antigen (HBsAg), Herpes Simplex viruses I and II, Herpes Virus Zoster, zytomegalovirus, Epstein-Barr virus, Papova viruses such as BK or JC virus, measles virus, rubella, influenza or parainfluenza viruses, etc. Viral subunits, such as a virus capsids, can also be determined, as long as such subunits are multivalent. Additionally, antigens need not be viral in nature to be multivalent, and among these may, for example, be included cells, immune complexes, membrane preparations, bacteria, proteins such as AFP or HCG, and the like.

Any monoclonal antibodies with medium to high affinity can be used (e.g., $\geq 10^7 M^{-1}$), such as IgG, IgE, IgM, and the like. Preferred among these are IgM and IgG, especially those of high affinity (e.g., $\geq 10^8 M^{-1}$).

The method of the present invention requires selection of at least two different antibodies with affinity towards two different epitopes on the same multivalent antigen, which are then immobilized. Selection of an antibody combination can normally be carried out by choosing each antibody from a different cell line.

There is no a priori method to assure that the two selected antibodies will not interfere with each other, either partially or completely. However, the invention is based on the discovery that enhanced resolution and decreased cross-reactivity can be obtained when using at least two different immobilized monoclonal antibodies; the method of how to choose them is a relatively straight-forward trial and error one, and can be accomplished by one skilled in the art without undue experimentation, once he/she knows the present discovery.

Nevertheless, some guidelines can be given: each antibody in the immobilized combination should exhibit as high a specificity for the multivalent antigen as possible. In other words, each antibody should be highly selective towards the antigen, and bind to it selectively in the presence of other, structurally similar antigens In addition, each antibody should have as high an affinity towards the antigen as possible. When these two general guides are followed a useful antibody combination can readily be found. Both of the guides or factors (specificity and affinity) can be optimized by carrying out binding experiments of soluble antibody supernatant with labelled (preferably radiolabelled) multivalent antigen. Two different antibodies showing high binding affinity are selected in a first step, and immobilized.

There is no a priori method to find which of the immobilized antibodies to use as the detectably labelled soluble antibody. The invention is based on the discovery that, once the correct one is determined, enhanced sensitivity is observed. The choice is carried out by trial and error, without undue experimentation.

As a guide, the ratio of binding observed in the immunometric assay when using multiple different immobilized antibodies with one of these as the soluble one, to using any one of them singly in the same assay, should normally be greater than 2, preferably greater than 5, and most preferably greater than 10.

Any variation of the sandwich assays, as long as it utilizes the combination of antibodies described, can be used in the present invention. Any automated technique which utilizes a sandwich immunoassay or variations thereof can of course be applied to the basic technique of the present invention. For example, such a technique is described in Goldie et al. U.S. Pat. No. 4,251,360.

In addition, the materials for use in the assay of the invention are ideally suited for the preparation of a kit. Such a kit may comprise a carrier means being compartmentalized to receive in close confinement one or more container means such as vials, test tubes and the like, each of said container means comprising one of the separate elements to be used in the method.

For example, one of said container means may comprise immunoabsorbent-bound different monoclonal antibodies. These antibodies may be bound to a separate solid phase immunoabsorbent or directly to the inner walls of a container. A second container may comprise soluble detectably labelled antibody in lyophilized form or in solution.

The carrier may also contain, in addition, a plurality of containers each of which comprises different, predetermined known amounts of antigen. These latter containers can then be used to prepare a standard curve into which can be interpolated the results obtained from the sample containing the unknown amount of antigen.

In using a simultaneous assay, all a user has to do is add, to the first container, a premeasured amount of an animal sample containing the measurable, yet unknown amount of antigen in a buffer and simultaneously add the contents of the labelled antibody present in the second container into the first container. Alternatively, all components are added to a separate container. After an appropriate time for incubation, solid phase is separated from the supernatant fluid, and the solid phase or the supernatant fluid are detected, as by radioactive counting or addition of an enzyme substrate, and color development.

Two monoclonal antibodies or substantial immunological equivalents thereof are utilized in applying the present assay to AFP. The first one, hereinafter AF01, is an antibody obtained from or having the identifying characteristics of an antibody obtained from cell line I-295. The second antibody, hereinafter referred to as AF03, is obtained from or has the identifying characteristics of an antibody obtained from cell line I-296. Moreover, two monoclonal antibodies or substantial immunological equivalents thereof are utilized in applying the present assay to hCG. The first one, hereinafter D1E8, is an antibody obtained from or having the identifying characteristics of an antibody obtained from cell line I-298. The second antibody, hereinafter referred to as FB03, is obtained from or has the identifying characteristics of an antibody obtained from cell line I-297. These cell lines have been deposited, on Mar. 29, 1984 at the Collection Nationale de Cultures de Micro-Organisms (CNCM), Institut Pasteur, 25 Rue du Docteur Roux, 75724 Paris, France. The identifying numbers of each of these cell lines are the accession numbers of the CNCM depository.

The AFP assay uses at least AF01 and AF03 on the solid phase and AF01 (or mixtures of AF01 and AF03) as the soluble labeled antibody. The HCG assay uses at least D1E8 and FB03 on the solid phase and FB03 (or mixtures of D1E8 and FB03) as the soluble labeled antibody.

Preparation and isolation of other appropriate antibodies and cells can be obtained by, for example, the methods described in Kennett, R. H., et al., *Monoclonal Antibodies. Hybridomas: A New Dimension in Biological Analyses,* Plenum Press, New York and London, 1982, especially pp. 363–418.

Having now generally described this invention, the same will be better understood by reference to certain specific examples which are incorporated herein for purposes of illustration only and are not intended to be limiting of the invention unless specified.

EXAMPLE 1

Assay for AFP

Production and Characterization of Monoclonal Antibodies

Six-week old BALB/c mice were injected with highly purified human AFP (Institut Behring, Marburg, W. Germany) according to several immunization procedures which varied the route and concentration of antigen and the interval between primary and secondary immunizations. Monoclonal antibodies AF01 and AF03 were produced by two protocols. The first generated antibody AF01, and involved subcutaneous (s.c.) injection of 15 microg AFP in Freund's complete adjuvant (FCA) as the initial dose, followed by 15 microg intraperitoneal (i.p.) injection in Freund's complete adjuvant (FIA) two months later, followed one month later by 100 microg i.p. and 100 microg intravenously (i.v.) six, five and three days before cell fusion. Monoclonal antibody AF03 was produced from a second immunization where 50 microg was given one year (s.c., FCA), and three days (i.v.) prior to cell fusion.

Cell fusions were performed by incubating $5-10 \times 10^6$ SP2/0-Ag 14 mouse myeloma cells with $5-10 \times 10^7$ mouse spleen cells in 40% polyethylene glycol (mol wt, 1,000) (Bellet et al., *J. Clin. Endocr. Metab.* 56:530–533 (1983)). Hybridoma supernatants were tested for anti-AFP activity in a screening test using a polyethylene glycol (PEG) precipitation test with $^{125}$I-AFP. Positive hybrids were cloned twice by limiting dilution and ascites fluids produced by i.p. inoculation of nude mice with $5 \times 10^5$ hybridoma cells. Monoclonal anti-AFP antibody class and subclass were determined either by double antibody RIA with $^{125}$I-AFP and goat antiserum specific for mouse immunoglobulin M (IgM), IgA, IgG, IgG$_{2ab}$(Nordic, Tilburg, Netherlands), or by eluting the IgG bound to a protein A-sepharose column (Pharmacia Fine Chemicals, Piscataway, N.J.) at different pH values (as described by Ey et al., *Immunochemistry* 15:429–436 (1978)). Both were found to be of the IgG$_{2a}$ isotype. IgG$_{2a}$ was purified (2–4 mg/ml) from mouse ascites fluids by 50% ammonium sulfate precipitation followed by dialysis against 0.2M phosphate buffer pH 8 for 18 hours at 4° C. prior to Staph protein A affinity chromatography. The affinities of the anti-AFP monoclonal antibodies were determined with a double antibody RIA technique by measuring the binding of $^{125}$I-AFP in the presence of increasing amounts of AFP by Scatchard plot analysis. Monoclonal anti-AFP AF01 and AF03 had measured affinity constants of $1.6 \times 10^{10}$ and $5.0 \times 10^8$ liters/mole, respectively. Competitive inhibition studies established that each monoclonal antibody recognized a distinct and separate AFP determinant.

Development of Multisite Monoclonal Radioimmunoassay

Systematic testing of different combinations of monoclonal anti-AFP demonstrated that the most sensitive assay for serum AFP determination was a simultaneous sandwich monoclonal RIA (M-RIA) based on a mixture of AF01 and AF03 as bound antibodies on the solid phase support and AF01 as the radiolabelled indicator antibody. This assay used polystyrene beads (outer diameter, 0.64 cm, Precision Plastic Ball, Chicago, Ill.) coated with AF01 and AF03 antibodies. In the assay developed for AFP, it has been found that 20 microg/100 microl of an IgG$_1$, and 20 microg/100 microl of an IgG$_{2a}$ non-relevant monoclonal antibody (i.e. directed against another human protein) are needed for best performance. In addition, the "blockers" are placed in a tris-HCl buffer system, pH 7.2, with two different protease inhibitors, trysolol (0.1 microg/ml) and soybean trypsin inhibitor (0.2 microg/ml). Serum samples or AFP-positive standards (200 microl) and 130,000 cpm $^{125}$I-labelled AF01 (specific activity 10–16 microCi/g; 1 Ci = $3.7 \times 10^{10}$ becquerels) in 100 microl of buffer (50% fetal calf serum in PBS pH 7.2) were added simultaneously with the anti-AFP-coated beads. After an incubation at 45° C. for 1 hour, the solid phase support was then washed three times with distilled water, and radioactivity bound (cpm) was measured in a Beckman gamma well counter. Assay standards consisted of either purified AFP diluted in pooled normal human serum or commercial AFP standard (Abbott Laboratories, North Chicago, Ill.).

Conventional Radioimmunoassay for Alpha-Feto Protein

The results of a conventional polyvalent RIA were compared in selected samples with the M-RIA of the invention for AFP. The RIA-GNOST, AFP-TACHISORB (Behring, Marburg) commercial system was used. This assay has a lower limit of sensitivity of 1.5 ng/ml and was performed according to the manufacturer's instructions.

Subjects

From the serum bank in the Gastrointestinal Unit at the Massachusetts General Hospital, sera from 250 normal subjects was chosen; 536 with miscellaneous liver and other disease controls consisting of 27 with various tumors (colon (13), pancreas (7), breast (2), and lung (5)), 13 with HBsAg positive biopsy proven cirrhosis, 10 with biopsy proven HBsAg negative chronic active hepatitis and 17 with non-B acute viral hepatitis were also chosen. The remaining 469 included other disease controls such as pneumonia, ulcerative colitis, coronary artery disease, hemodialysis patients, inflammatory bowel disease, etc. 477 chronic HBsAg carriers of adw, ayw, adr and ayr subtypes identified through routine screening of blood donors were also chosen. Sera from patients with HBsAg positive and negative hepatocellular carcinoma (HCC) from the Far East and Africa, including chronic HBsAg carriers with and without liver disease from the same region of the world were also studied.

In addition, serum samples from 60 patients were obtained from Institut Gustave Roussy (France). The diagnosis, confirmed by review of operative notes and pathology reports were as follows: hepatocellular carcinoma, HBsAg status unknown (8); children with hepatoblastoma (3); placental tumors (18); testicular; tumors (8); colorectal carcinoma (9); medullary thyroid carcinoma (2); lung metastases of unknown origin (2) and carcinomas of the esophagus (1), breast (6) and lung (1).

Immunometric Monoclonal Assay

A sensitive simultaneous sandwich assay was developed when a mixture of AF01 and AF03 were used on the solid phase support and $^{125}$I-labelled AF01 was employed as the indicator antibody. The sensitivity of the assay (1 hour incubation at 45° C.) was approximately 0.5 ng/ml, as determined by a signal-to-noise ratio (S/N) of greater than 2.5 (defined as cpm measured in the experimental sample divided by the mean cpm of 10 negative controls). The standard curves from two different assays are shown in FIG. 3. The concentration range of AFP standard varied between 1.5 and 200 ng/ml. The AFP standard curve is linear in the 1.5 to 40 ng/ml range. Absolute serum AFP concentrations in experimental samples were determined from serial dilutions and by use of the AFP standard curve.

Results of Serum AFP Values

Sera from 1,747 individuals were studied. Each specimen was analyzed in duplicate on two separate occasions. The results are shown in Table 1.

Thus, the majority of HCC patients, particularly those who were HBsAg chronic carriers, had markedly high levels of AFP by the one hour simultaneous sandwich assay. These findings are in striking contrast to serum AFP levels in patients with other malignant diseases which excludes tumors of the testis, where only one of 68 with a value greater than 100 ng/ml were found (Table 1). That patient developed an esophageal carcinoma and, at the time of study, his serum AFP level was 280 ng/ml. Thus, the M-RIA of the invention has a remarkable specificity for AFP-producing tumors, namely HCC from various regions of the world.

To determine if absolute serum AFP values measured by this M-RIA were comparable to those obtained by a

TABLE 1

Percentage of Positive AFP Values by a One Hour Monoclonal Immunometric Assay in Healthy Subjects and Various Malignant and Non-Malignant Diseases

| Category | No. of Subjects | AFP Levels (ng/ml) | | | | | | | |
|---|---|---|---|---|---|---|---|---|---|
| | | 0-5 | 5-10 | 10-20 | 20-40 | 40-60 | 60-80 | 60-100 | >200 |
| Healthy subjects | 450 | 100% | — | — | — | — | — | — | — |
| Miscellaneous* | 536 | 96.4% | 2.4% | 0.93% | — | — | — | — | — |
| HBsAg Pos. chronic carriers (subtypes adw, ayw and ayr, adr) | 477 | 98.1% | 0.84% | 1% | — | — | — | — | — |
| HBsAg Pos. chronic carriers (Africa) | 77 | 98% | 2% | — | — | — | — | — | — |
| HBsAg Pos. chronic carriers (Far East) | 10 | 100% | — | — | — | — | — | — | — |
| A.H., CAH HBsAg Pos. (Far East) | 24 | 95.8% | — | — | — | — | — | — | 4.1%(1) |
| Cirrhosis HBsAg Pos. (Far East) | 20 | 95% | — | — | — | 5%(1) | — | — | — |
| HCC HBsAg Pos. (Africa) | 28 | 10.7% | — | 3.6%(1) | 3.6%(1) | — | — | — | 82%(23/28) |
| HCC HBsAg Pos. (Far East) | 57 | 21% | — | — | — | — | — | — | 79%(45/57) |
| HCC** (France) | 11 | — | — | — | — | — | — | — | 100% |
| HCC HBsAg Neg.= | 16 | 62% | — | — | — | — | — | — | 38%(6) |
| Other tumors*** | 41 | 92.6% | — | 2.4%(1) | 2.4%(1) | — | — | — | 2%(1) |
| TOTAL | 1,747 | | | | | | | | |

*See prior text, supra
=p < 0.001 vs HBsAg Positive
**3 of 11 are children with hepatoblastoma
***Includes tumors of placenta, colon, rectum, esophagus, breast, medullary thyroid, lung and of unknown origin (2).
( ) is the number of subjects The results may be summarized as follows: (i) All healthy subjects (450) had AFP values below 5 ng/ml. (ii) Of 564 HBsAg chronic carriers from three different continents, 98.2% had AFP levels below 5 ng/ml and 100% were below 20 ng/ml. (iii) In 536 patients from the United States with nonmalignant disorders of the liver and other diseases (including carcinomas of gastrointestinal tract, breast and lung), 96.4% had an AFP level below 5 ng/ml, 99.6% below 20 ng/ml and 100% below 100 ng/ml. (iv) AFP levels were found to be below 5 ng/ml in 23 of 24 patients (95.8%) from the Far East with acute or chronic hepatitis; only one had an AFP above 200 ng/ml (326 (ng/ml). (v) In 20 cirrhotic patients from the Far East, 95% had an AFP below 5 ng/ml and only one had an AFP level greater than 40 ng/ml (57 ng/ml).

In contrast, AFP levels from 112 patients with HCC are depicted in FIG. 4. The absolute values varied widely and ranged from 240 ng/ml to >200,000 ng/ml. It is noteworthy that 82% of HBsAg positive HCC from Africa and 79% from the Far East had AFP levels >200 ng/ml. In contrast, only 6/16 (38%) of HBsAg negative HCC from the Far East were reactive for AFP levels >200 ng/ml (p<0.001). Finally, a smaller group of 11 HCC from France, including three children with hepatoblastoma, were reactive for AFP greater than 200 ng/ml.

conventional polyvalent antibody RIA, seventeen patients with various tumors were studied. As shown in Table 2, the polyvalent and M-RIAs were quite comparable with respect to the absolute serum AFP concentration and over a wide range of AFP levels. Patients with very high levels of AFP were also studied since this assay employs a simultaneous sandwich mode, and it was interesting to examine the magnitude of the "hook effect" as shown by the representative example in FIG. 5. This patient has an AFP level of >1 mg/ml. Despite the exceedingly high level of AFP measured in some patients, no false negative value due to the "hook effect" has been observed to date.

Discussion

This example shows the development of a simultaneous sandwich RIA using a combination of two immobilized high affinity monoclonal antibodies directed against two separate epitopes of human AFP. This M-RIA is approximately four to ten times more sensitive than commercially available conventional polyvalent RIAs; it has a lower level of sensitivity of approximately 0.5 ng/ml. The assay is technically convenient and rapid, involving the simultaneous addition of all reagents and a one-hour incubation at 45° C. The so-called "hook effect" previously described for "one step" immunoassays (Nomura, et al., *J. Immunol.*

56:13-17 (1983)) was also observed for high AFP values (i.e., above 3,000 ng/ml). However, this phenomenon did not lead to false negative AFP results but only required additional dilutions to accurately measure the absolute AFP value from the standard curve.

One of the major problems with current polyvalent AFP assays is their limitation in discriminating between AFP-producing carcinomas (especially HCC) and various benign liver diseases. Serum AFP levels have been reported to be above 20 ng/ml in 67% to 82% of HCC (Ruohslati et al., Br. Med. J. 393:527-529 (1974), Wepsic, H. T., et al., Gastroenterology 77:787 (1979)). However, given the limited specificity of the polyvalent assays, AFP elevations greater than 20 ng/ml have been observed in 31% to 40% of patients with acute and chronic hepatitis and 8% to 33% of patients with cirrhosis (Ruohslati et al., op. cit., Wepsic, et al., op. cit., Alpert et al., Gastroenterology 74:856 (1978)). In one study, serum AFP levels greater than 100 ng/ml were reported in 19% of patients with acute hepatitis and 5% with cirrhosis (Alpert et al., op. cit.).

In this example, 86/116 (76.7%) of HCC patients had AFP serum levels above 20 ng/ml, with 85/112 (75.8%) having leads above 100 ng/ml, a finding consistent with other reports (Wepsic et al., supra). If those patients with HCC who were also HBsAg positive carriers are considered, 80% had AFP levels greater than 200 ng/ml. In patients with various types of malignancy, the AFP levels by both M-RIA and C-RIA were quite comparable. However, most significant was the finding that, compared to previous studies with polyvalent antibodies, the incidence of AFP elevation using the M-RIA of the invention was extremely low in normal individuals and a number of different disease categories. Thus, no healthy subject had a level above 5 ng/ml, whereas other reports have shown 75% of normal human sera to have AFP levels greater than 5 ng/ml (Ruoshlati et al., Nature 235:161-162 (1972) and Ruoshlati et al., Int. J. Can., 8:374-383 (1971)). It is also noteworthy that 98.1% of HBsAg chronic carriers had a serum AFP level below 5 ng/ml and 100% had levels below 20 ng/ml. It was striking that 96.4% of patients with miscellaneous liver disorders and other disease controls had AFP values below 5 ng/ml with 99.6% below 20 ng/ml. More surprising was the finding that in cirrhotic patients (regardless of the etiology of the cirrhosis or their geographical origin), only 3% (1/33) had an AFP level above 20 ng/ml and none had levels above 100 ng/ml. In the acute or chronic active hepatitis patients studied, only 1.9% (1/51) had an AFP level above 20 ng/ml. Thus, the M-RIA of the invention demonstrates remarkable specificity for AFP-producing tumors and, depending on the cutoff value for AFP positive results, these patients show little overlap with non-malignant liver disorders and other disease controls. Indeed, if one selects a cutoff value of 100 ng/ml only two of 1,185 disease controls (or 0.1%) exceeded that level.

The inventors speculate that the high AFP serum levels previously observed with conventional RIAs in benign liver diseases were due to the real production and secretion of AFP, or "AFP-like" proteins. Nevertheless, it is also possible that these high AFP values reflected artifacts due in part to the presence of cross-reactive molecules of "AFP-like" material. For example, previous studies by others have shown that "specific" antisera raised against purified human AFP were not cross-reactive with native albumin, even though this protein shares a large sequence homology with human AFP; however, such anti-AFP antisera reacted strongly with derivatives of human albumin. Thus, conventional polyvalent RIAs may yield false positive AFP values because of cross-reactions of polyvalent antisera with "AFP-like" material, including various albumin degradation products, which may occur in patients with inflammatory disorders of the liver. In contrast, the multisite M-RIA of the invention may fail to detect such cross-reactive proteins.

With this assay it is possible to use serum AFP as a screening assay for HCC. Since with the M-RIA of the invention the number of AFP positive sera (above 20 or 100 ng/ml) in chronic HBsAg carriers and in HBsAg positive acute and chronic hepatitis (with and without cirrhosis) was extremely low (99.9% of patients have AFP levels below 100 ng/ml), the M-RIA is useful as a screening test for the early diagnosis of hepatocellular carcinoma in high risk populations.

Comparative Example 1

In addition to AF01 and AF03, another anti-AFP monoclonal antibody (AF04) was also obtained. It was thus possible, by varying the combinations and permutations in the assay, to compare the effectiveness of the claimed combination with other combinations. Table 2 shows the results.

TABLE 2

| Exp. | Solid Phase Bound Antibody(ies) | Labelled Antibody(ies) | Results* |
|---|---|---|---|
| (1) | AF01 | AF03 | ++ |
| (2) | AF01 | AF04 | ++ |
| (3) | AF01 | AF01 + AF03 | + |
| (4) | AF01 | AF03 + AF04 | + |
| (5) | AF01 | AF01 | 0 |
| (6) | AF03 | AF01 | ++ |
| (7) | AF03 | AF01 + AF03 | ++ |
| (8) | AF03 | AF03 | 0 |
| (9) | AF01 + AF03 | AF01 | +++ |
| (10) | AF01 + AF03 | AF03 | ++ |
| (11) | AF01 + AF03 | AF04 | + |
| (12) | AF01 + AF03 | AF01 + AF03 | +++ |
| (13) | AF01 + AF03 | AF01 + AF04 | ++ |
| (14) | AF01 + AF03 | AF03 + AF04 | ++ |
| (15) | AF01 + AF04 | AF01 | 0 |
| (16) | AF01 + AF04 | AF04 | ++ |
| (17) | AF01 + AF04 | AF01 + AF03 | + |
| (18) | AF01 + AF04 | AF01 + AF04 | + |

*0 No binding at all
+ Poor binding
++ Good binding
+++ Very good binding

The results demonstrate quite clearly that antibodies AF01 and AF03 on the solid phase and antibody AF01 in the soluble labelled phase are the combination that gives best binding characteristics (Examples 9 and 12). The soluble labelled antibody AF01 can be complemented by another soluble labelled antibody, such as AF03 (Experiment 12). Of great interest is to note that the binary combination AF01/AF01 (Experiment 5) or AF03/AF03 (Experiment 8) gave no binding at all, and the combination AF01/AF03 (Experiment 1) or AF03/AF01 (Experiment 6) gave poor binding. The combination of AF03 with AF01 on the solid phase, however, unexpectedly provides exceptionally good binding (compare experiment 5 with experiment 9, or experiment 8 with experiment 12). In contrast, the combination of AF04 with AF01 on the solid phase provides no binding at all (compare experiment 5 with experiment 9).

EXAMPLE 2

Assay for HCG

Production and characterization of monoclonal antibodies

Two monoclonal antibodies identified as D1E8 and FB03, and directed against human chorionic gonadotropin (HCG) were selected after cell fusion experiments performed with spleen cells from mice injected with either beta subunit of HCG ( HCG, Boehringher, Mannheim) or a 37 amino acid synthetic polypeptide analogous to the carboxy terminus of HCG. The immunization procedures varied the route and concentration of the antigen, and the interval between primary and secondary immunizations. Hybridoma supernatants were tested for anti HCG activity in a screening test using a polyethylene glycol (PEG) precipitation test with $^{125}$I-HCG. Positive hybrids were cloned twice by limiting dilution, and ascites fluids were produced by i.p. inoculation of nude mice with $5\times10^5$ hybridoma cells. Monoclonal antibodies were purified from mouse ascites fluids by 50% ammonium sulfate precipitation followed by dialysis against 0.2M phosphate buffer pH 8 for 18 hours at 4° C. prior to staph protein A affinity chromatography. Competitive inhibition studies established that each monoclonal antibody recognized a distinct and separate HCG determinant. Inhibition studies carried on with both the native HCG and the carboxy terminal synthetic peptide analogue demonstrated that D1E8 and FB03 were directed against epitopes located respectively on the 1-109 and the 109-145 amino acid sequence of HCG.

Binding Experiments

In addition to D1E8 and FB03, another anti HCG monoclonal antibody identified as FB04 was also obtained. Binding experiments were carried out by coating on a solid phase support (polystyrene beads, outer diameter, 0.64 cm, Precision Plastic Ball, Chicago, Ill.) either each antibody alone or different mixtures of D1E8, FB03 and FB04. Then, 200 microl of $^{125}$I labelled HCG (30,000 cpm) were incubated with the precoated antibody(ies) for 4 hr at 45° C. After washing and counting, the percentage of labelled HCG bound was calculated. FIG. 6 illustrates the results. B is defined as cpm bound and T as total cpm added. These results demonstrate quite clearly that a mixture of D1E8 and FB03 binds HCG ar better that D1E8 or FB03 alone, i.e. a synergistic effect is obtained.

Development of Multisite Monoclonal Immunoassay

Systematic testing of different combinations of monoclonal anti HCG was performed with D1E8, FB03 or a mixture of D1E8 and FB03 either on the solid phase or as labelled antibody(ies). After coating of the antibody(ies) on the solid phase support, 200 microl of HCG containing serum (100 nanogram/milliliter) and 100 microl of labelled antibody(ies) (130,000 cpm) were added. After a 4 hour incubation, washing and counting, the binding of the labelled antibody(ies) was determined. No binding was observed with D1E8 on the solid phase support and as soluble labelled antibody. Likewise, no binding was observed with FB03 on the solid phase support and as soluble labelled antibody. In contrast, good binding was observed with a mixture of D1E8 and FB03 on the solid phase support and FB03 as soluble labelled antibody. This combination led to the development of a totally specific monoclonal radioimmunoassay for HCG.

EXAMPLE 3

Detection of Dengue 1 Virus in Serum

Dengue infection is one of the most common arbovirus illnesses in man and is transmitted from person to person by the Ades mosquito. There are four different viral strains (1, 2, 3, and 4), all of which are group B arboviruses. This illness is characterized by high fever, muscle aches, severe fatigue, and headaches, and often accompanied by a rash. It is estimated that 8 million known cases occur per year on a worldwide basis. This viral infection is most common in tropical areas of the world. The virus circulates in blood during illness, since it is transmitted from person to person by the mosquito vector. Denque virus is described, for example, in Petersdorf, et al., eds., *Harrison's Principles of Internal Medicine*, 10th Ed., McGraw-Hill, New York, pp. 1146-47, 1153-54, and in references cited therein.

There is a clinical need to establish very sensitive and specific immunoassays to detect and measure the virus in the blood in an attempt to diagnose this serious viral infection and to prevent spread of the illness by mosquito control.

Mice were immunized with purified dengue 1 virus to produce a large library of monoclonal antibodies. Of 120 antibodies produced, eight were found to be specific for the dengue 1 serotype. The other 122 reacted not only with dengue 1, but also with dengue serotypes 2, 3 and 4, as well as with other flaviviral strains.

Various combinations of these 8 anti-dengue monoclonal antibodies were evaluated as taught in the present specification, either bound to a solid-phase support or as radiolabeled indicator probes, as described for AFP and HCG in examples 1 and 2. Table 3 shows the results of two such antibodies. The other six antibodies gave inferior results compared to antibodies 4F4 and 3F5.

Beads coated with antibodies alone or in combination were incubated with 200 $\mu$l of serum containing a fixed concentration of dengue 1 virus at 1.6 ng/ml. The beads were washed after a 16-hour incubation at 20° C., and 200 $\mu$l of radiolabeled antibody (150,000 CPM) were added, followed by a four-hour incubation at 20° C. The beads were washed and the radioactivity bound to the bead determined.

As can be observed from Table 3, the combination of 4F4 on the bead and 4F4 on the radiolabeled antibody gave a S/N of 11.15 (S/N is a measure of specific binding and is defined in this example as the CPM bound in the sample containing 1.6 ng/ml of dengue 1 virus in serum divided by the CPM bound in dengue 1 negative control serum; S/N>2.0 is considered positive). Another combination, using monoclonal antibody 3F5, where the capture and radiolabeled indicator antibody are again the same, gave better results (S/N=127.33).

However, when antibodies 4F4 and 3F5 were combined on the beads, with 3F5 as the radiolabeled probe, the binding of dengue virus became unexpectedly high at a S/N of 4,197. Thus, this assay design results in a striking increase in sensitivity, achieved by using a combination of two monoclonal antibodies on the solid phase with one of these antibodies as the soluble-phase-labeled antibody.

Viral titration studies reveal that this assay format detects as little as 50 pg/ml of dengue 1 in serum. Heretofore, it was not possible to measure such a low level of virus in human serum. Indeed, it had not been possible to reliably measure dengue virus at all. By means of the present invention, then, a reliable, sensitive, accurate and reproducible serodiagnostic immunoassay for viral infections in animals, including man, has been achieved.

This example demonstrates, in a totally different biologic system, that when antibody A (3F5) and B (4F4) are bound to a solid-phase support and antibody A (3F5) is labeled, unexpected and surprising sensitivity is achieved, compared to other combinations. This is further evidence of the broad applicability of the present invention to multivalent antigen immunoassays. Monoclonal antibody 4F4 is produced by hybridoma strain $D_1 4F4$. Monoclonal antibody 3F5 is produced by hybridoma strain $D_1 3F5$.

TABLE 3

Improvement in dengue 1 assay sensitivity using anti-dengue monoclonal antibodies either alone or in combination

| EXP | Bead Capture Ab | 125 [I]-labeled Probe | S/N | CPM Bound |
|---|---|---|---|---|
| 1 | 4F4 | 4F4* | 11.15 | 256.5 |
| 2 | 4F4 | 3F5* | 346.90 | 13,874 |
| 3 | 3F5 | 4F4* | 12.82 | 538.5 |
| 4 | 3F5 | 3F5* | 122.35 | 7,769.5 |
| 5 | 4F4/3F5 | 4F4* | 537.20 | 4,566 |
| 6 | 4F4/3F5 | 3F5* | 4,197.05 | 35,675 |

S/P > 2.0 is considered positive (see text). The concentration of dengue 1 virus in serum was fixed at 1.6 ng/ml.

What is claimed as new and intended to be protected by Letters Patent of the United States is:

1. An immunometric assay for a multivalent antigen in a sample, comprising:
   (a) forming a mixture of said sample with multiple immobilized monoclonal antibodies against different epitopes on said antigen, and incubating said mixture for a time and under conditions sufficient to allow said antigen in said sample to bind to said multiple immobilized monoclonal antibodies;
   (b) adding to said mixture after said incubation of step (a) a detectably labeled monoclonal soluble antibody which is identical to one of said multiple immobilized monoclonal antibodies, and incubating the new resulting mixture for a time and under conditions sufficient to allow said detectably labeled monoclonal soluble antibody to bind to said antigen;
   (c) separating detectably labeled monoclonal antibody bound to said antigen from detectably labeled monoclonal soluble antibody; and
   (d) detecting either said detectably labeled monoclonal antibody bound to said antigen, or detecting detectably labeled monoclonal soluble antibody not bound to said antigen;
wherein any one of said multiple immobilized monoclonal antibodies shows, by itself, substantially less binding towards said antigen in said immunometric assay, when used with itself or another monoclonal antibody in soluble labeled form, than when used with multiple immobilized monoclonal antibodies in combination.

2. The assay of claim 1, wherein said antigen is alpha-fetoprotein.

3. The assay of claim 1, wherein said antigen is human chorionic gonadotropin.

4. The assay of claim 2, wherein said multiple immobilized monoclonal antibodies comprise at least two immobilized monoclonal antibodies present on the same solid surface, the first of said antibodies having the binding specificity of antibody AF01 obtained from the hybridoma cell line I-295; and the second of said antibodies having the binding specificity of antibody AF03 obtained from hybridoma cell line I-296.

5. The assay of claim 3, wherein said multiple immobilized monoclonal antibodies comprise at least two immobilized monoclonal antibodies present on the same solid surface, the first of said antibodies having the binding specificity of antibody FB03 obtained from the hybridoma cell line I-297; and the second of said antibodies having the binding specificity of antibody D1E8 obtained from hybridoma cell line I-298.

6. A kit useful for the detection of a multivalent antigen in a sample comprising a carrier being compartmentalized to receive in close confinement therein one or more containers wherein
   (a) a first container contains multiple monoclonal antibodies against different epitopes on said antigen, immobilized on an insoluble solid phase;
   (b) a second container contains detectably labelled monoclonal soluble antibody which is identical to one of said multiple immobilized antibodies.

7. The kit of claim 6 wherein said antigen is alphafetoprotein or human chorionic gonadotropin.

8. The kit of claim 6 wherein said first container contains antibodies derived from cell lines I-295 and I-296 and wherein said second container contains antibody derived from cell line I-295.

9. The kit of claim 6 wherein said first container contains antibodies derived from cell lines I-297 and I-298 and wherein said second container contains antibody derived from cell line I-297.

10. An insoluble immunological reagent support for use in an immunometric assay for a multivalent antigen selected from the group consisting of alpha-fetoprotein and human chorionic gonadotropin, which comprises an insoluble support comprising at least two different immobilized monoclonal antibodies against said antigen, wherein said monoclonal antibodies are bound to said insoluble support in a non-interfering manner.

11. The reagent of claim 10 wherein one of said antibodies is derived from hybridoma cell line I-295, which secretes antibody AF01, and the other is derived from hybridoma cell line I-296, which secretes antibody AF03.

12. The reagent of claim 10 wherein one of said antibodies is derived from hybridoma cell line I-297, which secretes antibody FB03, and the other is derived from hybridoma cell line I-298, which secretes antibody D1E8.

* * * * *